United States Patent [19]

Kageyama et al.

[11] Patent Number: 5,484,725

[45] Date of Patent: Jan. 16, 1996

[54] **NORBORNANE TYPE ESTER HYDROLASE FROM *ACETOBACTER PASTEURIANUS***

[75] Inventors: Bunji Kageyama, Ibaraki; Masanori Nakae, Toyonaka; Shigeo Yagi, Takatsuki, all of Japan

[73] Assignee: Shionogi & Co., Ltd., Osaka, Japan

[21] Appl. No.: 232,519

[22] Filed: Apr. 22, 1994

[30] Foreign Application Priority Data

Apr. 22, 1993 [JP] Japan .................................. 5-096286

[51] Int. Cl.$^6$ .............................. C12N 9/18; C12N 9/16
[52] U.S. Cl. .......................... 435/197; 435/196; 435/823
[58] Field of Search ..................................... 435/196, 823, 435/197

[56] References Cited

U.S. PATENT DOCUMENTS

| 4,075,405 | 2/1978 | Takahashi et al. | 536/55.1 |
|---|---|---|---|
| 5,124,462 | 6/1992 | Ohtani et al. | 549/463 |
| 5,270,206 | 12/1993 | Saccomano | 435/280 |

FOREIGN PATENT DOCUMENTS

| 0387068 | 12/1990 | European Pat. Off. . |
|---|---|---|
| 0422768 | 4/1991 | European Pat. Off. . |
| 0428302 | 5/1991 | European Pat. Off. . |
| 0529424 | 3/1993 | European Pat. Off. . |

OTHER PUBLICATIONS

Meltz et al., Tetrahedron Lett. 33:1201–1202 (1992).
Th. Oberhauser et al., "Enzymatic Resolution of Norbornane–Type Esters", *Tetrahedron*, 43 pp. 3931–3944 (1987).

M. Narisada et al., "Synthesis and in Vitro Activity of Various Derivatives of a Novel Thromboxane Receptor Antagonist, (±)-(5Z)-7-[3-endo-[(Phenylsulfonyl) amino] bicyclo [2.2.1] hept–2–exo–yl] heptenoic Acid", *J. Med. Chem.*, 31, pp. 1847–1854 (1988).

*Primary Examiner*—Robert A. Wax
*Assistant Examiner*—Eric Grimes
*Attorney, Agent, or Firm*—Fish & Neave; James F. Haley, Jr.; Kevin R. Hansbro

[57] ABSTRACT

A norbornane type ester hydrolase that enantio-selectively hydrolyzes a (±)-exo-norbornane type ester represented by Formula I is provided:

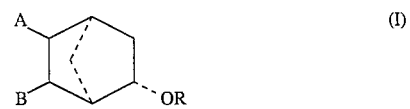

wherein R is acyl, and A and B are hydrogens, respectively, or where A and B are absent, resulting in a carbon-carbon double bond between the carbons to which A and B are attached in Formula I. The norbornane type ester hydrolase has an optimal pH of approximately 8 and a stable pH range of approximately 6 to 8.

5 Claims, 2 Drawing Sheets

NORBORNANE TYPE ESTER HYDROLASE FROM *ACETOBACTER PASTEURIANUS*

BACKGROUND OF THE INVENTION

1. Field of the Invention

The present invention relates to a novel norbornane type ester hydrolase that enantio-selectively hydrolyzes a (±)-exo-norbornane type ester to produce optically active norborneol; a structural gene of the norbornane type ester hydrolase; an expression vector including the structural gene; a transformant including the expression vector; and a production method for the norbornane type ester hydrolase using the transformant.

2. Description of the Related Art

Several methods for preparing norborneol are known in the art. The known methods are classified into chemical and biological methods. For example, the following chemical method is known. Norbornene used as a starting material is allowed to react with an organic acid to produce a norbornane type ester compound. The ester compound is chemically hydrolyzed to produce norborneol. In this chemical method, four kinds of stereoisomers of norborneol (i.e., (+)-endo-norborneol, (−)-endo-norborneol, (+)-exo-norborneol and (−)-exo-norborneol) are simultaneously produced. Therefore, a complicated separation is further required to obtain an optically active norborneol.

Another production method for norborneol using the following biological method is also known. Norbornene used as a starting material is allowed to react with an organic acid to produce a norbornane type ester compound. The ester compound is allowed to react with an enzyme, or to come in contact with microorganisms producing such an enzyme, thereby hydrolyzing the ester compound to obtain norborneol. With regard to this biological method, Oberhauser et al. reported a method for producing (−)-norborneol from (±)-norbornyl acetate by using a lipase derived from *Candida cylindraceae* (Th. Oberhauser et al., Tetrahedron, 43, 3931–3941, 1987). The method using the lipase, however, has a low selectivity and the produced norborneol has a low optical purity.

Japanese Laid-Open Patent Publication No. 2-273196 discloses an optical resolution method of a racemic mixture using a biological hydrolysis reaction, in which an inhibitor for selectively inhibiting the hydrolysis reaction of one of the enantiomers is used in the reaction. Such a method can be employed to prepare optically active norborneol. In this method, however, it is necessary to perform a screening of inhibitors to obtain an inhibitor that is useful in the selection of the optically active norborneol. Further, it is required to remove the inhibitor after the reaction. As a result, such a method is disadvantageously complicated.

SUMMARY OF THE INVENTION

The norbornane type ester hydrolase of this invention enantio-selectively hydrolyzes a (±)-exo-norbornane type ester represented by Formula I:

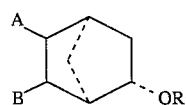

wherein R is acyl, and A and B are hydrogens, respectively, or where A and B are absent, resulting in a carbon-carbon double bond between the carbons to which A and B are attached in Formula I;

the norbornane type ester hydrolase having an optimal pH of approximately 8 and a stable pH range of approximately 6 to 8.

A norbornane type ester hydrolase of this invention enantio-selectively deacetylates a (±)-exo-norbornyl acetate represented by Formula II:

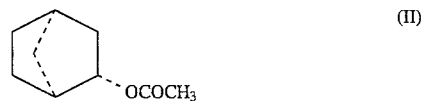

the norbornane type ester hydrolase having an optimal pH of approximately 8 and a stable pH range of approximately 6 to 8.

In one embodiment, a norbornane type ester hydrolase of this invention is derived from a bacterium of the genus Acetobacter, preferably, *Acetobacter pasteurianus*.

In one embodiment, the above-mentioned *Acetobacter pasteurianus* is *Acetobacter pasteurianus* ATCC 12873.

A norbornane type ester hydrolase of this invention comprises an amino acid sequence from Met in the 1 position to Ala in the 388 position of SEQ ID No. 1.

The present invention includes a DNA sequence encoding the norbornane type ester hydrolase having the above-mentioned amino acid sequence.

In one embodiment, the above-mentioned DNA sequence comprises a base sequence from A in the 1 position to C in the 1164 position of SEQ ID No. 1.

The present invention includes an expression vector having the above-mentioned DNA sequence.

The present invention includes a transformant produced by introducing the above-mentioned expression vector into a host.

In one embodiment, the host is *E. coli*.

A production method for a norbornane type ester hydrolase of this invention comprises the steps of, culturing the above-mentioned transformant in a culture medium, and recovering the produced norbornane type ester hydrolase from the culture.

A production method for an optically active norborneol of this invention comprises the step of, allowing a (±)-exo-norbornane type ester to come in contact with the above-mentioned norbornane type ester hydrolase; the (±)-exo-norbornane type ester being represented by Formula I:

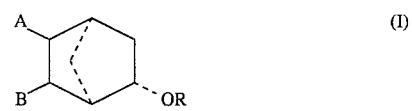

wherein R is acyl, and A and B are hydrogens, respectively, or where A and B are absent, resulting in a carbon-carbon double bond between the carbons to which A and B are attached in Formula I.

In one embodiment, R in Formula I is acetyl, and A and B are hydrogens, respectively.

Thus, the invention described herein makes possible the advantages of (1) providing a novel norbornane type ester hydrolase that can produce optically active norborneol with a high purity; and (2) providing a DNA sequence for encoding the norbornane type ester hydrolase, an expression vector including the DNA sequence, a transformant including the expression vector and a production method for the norbornane type ester hydrolase using the transformant.

These and other advantages of the present invention will become apparent to those skilled in the art upon reading and understanding the following detailed description with reference to the accompanying figures.

DESCRIPTION OF THE PREFERRED EMBODIMENTS

Figure 1:
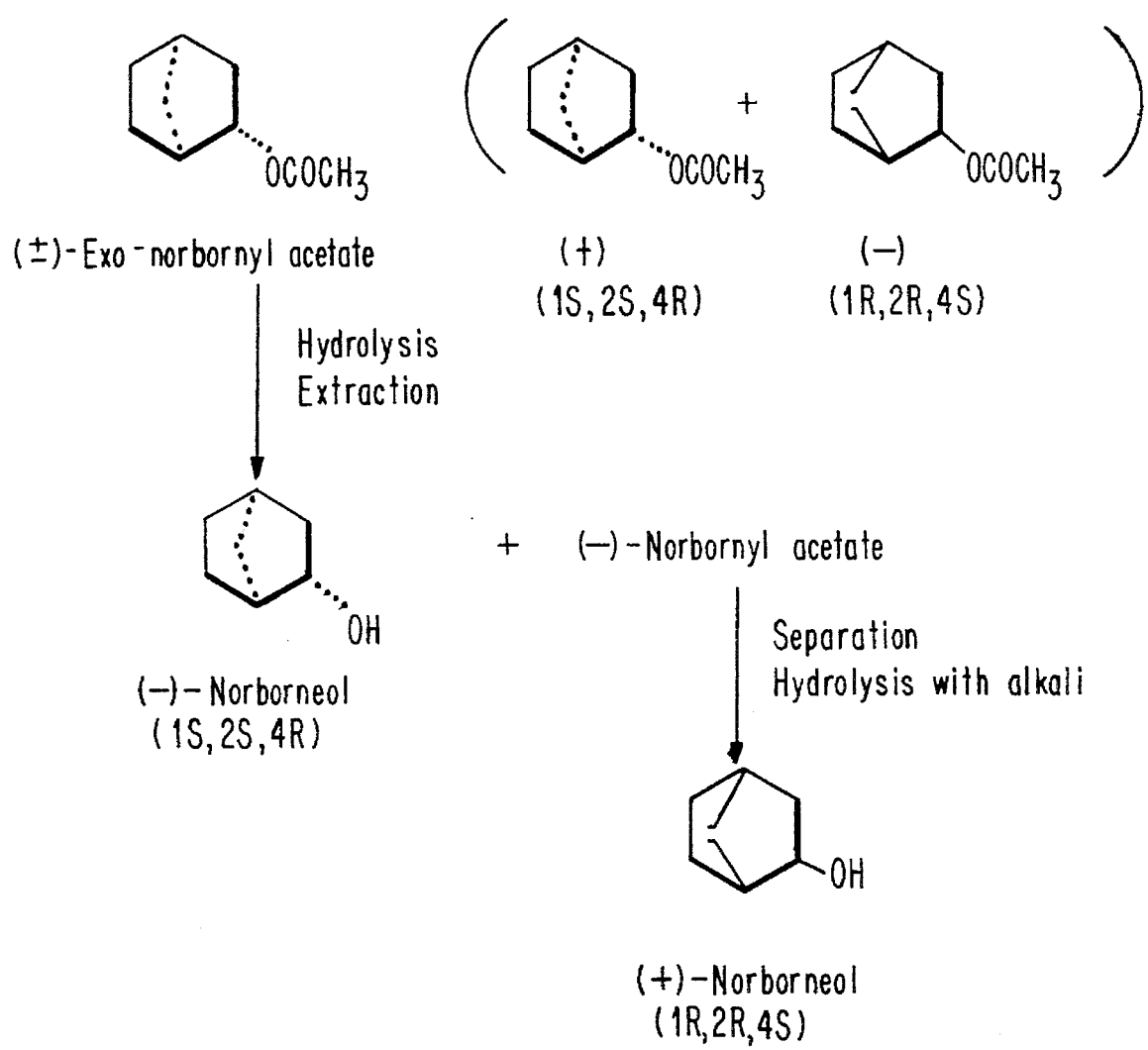
FIG. 1 shows enantio-selective deacetylation of (±)-exo-norbornyl acetate by a norbornane type ester hydrolase of the present invention.

The present inventors have conducted various studies to obtain optically active norborneol with a high purity from a racemic mixture of norbornane type ester compounds. As a result, it was found that a strain of *Acetobacter pasteurianus* ATCC 12873 produces a norbornane type ester hydrolase, and that the hydrolase selectively deacetylates (±)-exo-norbornyl acetate as shown in FIG. 1 to produce optically active norborneol with a high optical purity. The present inventors have further determined a DNA sequence for encoding the norbornane type ester hydrolase in the genomic DNA of the strain, thereby achieving the present invention.

The term "optically active norborneol" as used herein means one of the compounds (+)-norborneol and (−)-norborneol. A preferable optically active norborneol is (−)-norborneol.

The term "a norbornane type ester" as used herein means an ester of norborneol or an ester of norborneol derivatives. The (±)-exo-norbornane type ester used in the present invention is represented by Formula I:

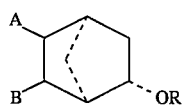

(I)

wherein R is acyl; and A and B are hydrogens, respectively, or where A and B are absent, resulting in a carbon-carbon double bond between the carbons to which A and B are attached in Formula I.

In Formula I, the acyl is an aliphatic acyl, cycloalkylcarbonyl or arylcarbonyl. The aliphatic acyl has 2 to 10 carbon atoms, and preferably 2 to 7 carbon atoms. The aliphatic acyl includes formyl, acetyl, propionyl, butyryl, isobutyryl, pentanoyl and hexanoyl, and is more preferably formyl, acetyl, propionyl or isobutyryl. The cycloalkylcarbonyl preferably has 4 to 10 carbon atoms, and preferably 4 to 7 carbon atoms. The cycloalkylcarbonyl includes cyclopropanecarbonyl, cyclobutanecarbonyl, cyclopentanecarbonyl and cyclohexanecarbonyl. The arylcarbonyl preferably has 7 to 11 carbon atoms and includes benzoyl, p-toluoyl and naphtoyl.

The compounds of Formula I are commercially available or alternatively can be easily chemically synthesized with methods known in the art. For example, a desired (±)-exo-norbornane type ester represented by Formula I can be produced in a high yield by reacting norbornene with an appropriate organic acid such as formic acid, acetic acid, propionic acid and lactic acid in the presence of an acid catalyst; or by causing a Dieis-Alder reaction between a vinyl ester of an appropriate organic acid and cyclopentadiene.

The norbornane type ester hydrolase of the present invention is produced from bacteria of genus Acetobacter, preferably *Acetobacter pasteurianus* ATCC 12873. This strain is available from American Type Culture Collection (ATCC).

(1) Culture conditions:

No special medium is required for the cultivation of the above-mentioned bacteria, and any of the various conventional types of culture mediums can be used. For example, a medium containing glucose, peptone, yeast extract, various salts and the like can be used. The appropriate medium pH is 5 to 9, and preferably approximately 7. The appropriate medium temperature is 25° to 30° C., and preferably approximately 28° C. The bacteria are cultured, for example, aerobically with stirring or shaking. The norbornane type ester hydrolase of the present invention is produced intracellularly.

(2) Purification of the enzyme:

One or a combination of known techniques can be used to isolate and purify the norbornane type ester hydrolase from the culture. For example, the culture is centrifuged to collect bacteria cells therein. The cells of the collected bacteria are disrupted, and the resultant is centrifuged again to obtain a supernatant as a crude enzyme solution. The crude enzyme solution is purified by an appropriate method to obtain the norbornane type ester hydrolase. For example, the crude enzyme solution is subjected to a DEAE Sepharose chromatography and then to polyacrylamide gel electrophoresis to isolate a band exhibiting an enzymatic activity, thus, obtaining the norbornane type ester hydrolase.

(3) Measurement of the enzymatic activity:

The norbornane type ester hydrolase reacts with p-nitrophenyl acetate, in addition to exo-norbornane type ester, as a substrate to produce a colored material, p-nitrophenol. Since p-nitrophenol can be detected spectrophotometrically, the enzymatic activity of the norbornane type ester hydrolase is measured by the following p-nitrophenyl acetate method in which p-nitrophenyl acetate (pNPA) is used as a substrate.

p-Nitrophenyl acetate method: an enzyme solution is added to a 0.1M phosphate buffer (pH 7.0) including 0.02% p-nitrophenyl acetate and 5 mM magnesium chloride so as to achieve a final volume of 3 ml. The reaction is conducted at a temperature of 30° C. for 20 minutes. The absorbance of p-nitrophenol released into the reaction mixture by the enzymatic reaction is measured at 400 nm. The amount of the enzyme producing 1 μmole of p-nitrophenol for 1 minute is defined as 1 unit (U).

(4) Properties of the enzyme:

The enzymatic properties and protein chemical properties of the norbornane type ester hydrolase of the present invention are as follows:

(a) Enzymatic action and substrate specificity:

Various kinds of the (±)-exo-norbornane type esters respectively comprising formyl, acetyl, propionyl, n-butyryl or isobutyryl as the acyl R in formula I were allowed to come in contact with an enzyme solution, respectively as a substrate. Each of the obtained products was extracted with an equal volume of chloroform. The extract was analyzed by gas chromatography using a column for optical resolution (produced by J & W Scientific). (−)-Norborneol was selectively produced in all the extracts. As is apparent from this result, the enzyme is a hydrolase that enantio-selectively hydrolyzes the (±)-exo-norbornane type ester to produce an optically active norborneol, i.e., (−)-norborneol. In detail, referring to FIG. 1, (+)-(1S, 2S, 4R)-exo-norbornyl acetate is hydrolysed to the corresponding (−)-norborneol by the use of the present enzyme. The obtained (−)-norborneol can be converted to (+)-d-norcamphor by oxidation. The remaining (−)-(1R, 2R, 4S)-exo-norbornyl acetate can be hydrolysed to the corresponding (+)-norborneol by the use of an alkali. The obtained (+)-norborneol can be converted to (−)-d-norcamphor by oxidation.

(b) Optimal pH and stable pH range:

The enzymatic activity measurement described in item 3 was performed at various pH values by using p-nitrophenyl acetate as a substrate. As a result, the optimal pH for the reaction was found to be approximately 8.

The enzyme was allowed to stand for 1 hour at a temperature of 30° C. at various pH values. Then, the activity of the enzyme at each pH value was measured by the method described in item 3. The results revealed that the stable pH range of the enzyme is approximately 6 to 8.

(c) Optimal temperature and thermal stability:

The enzymatic activity of the present enzyme was measured by the method described in item 3 at various temperatures. The results revealed that the optimal temperature was approximately 50° C.

The enzyme was allowed to stand in a phosphate buffer for 2 hours at pH 7.0 at various temperatures. Then, the activity of the enzyme was measured using the method described in item 3. The results revealed that the present enzyme was stable at a temperature up to 40° C. under the above-mentioned conditions.

(d) Effect of inhibitors:

The present enzyme was allowed to stand in phosphate buffers respectively including various inhibitors (5 mM) at pH 7.0 for 2 hours. Then, the activity of the enzyme was measured by the method described in item 3. The results revealed that the present enzyme was completely inhibited by phenylmethylsulfonylfluoride (PMSF).

(e) Molecular weight:

The molecular weight of the present enzyme was measured by SDS-PAGE (SDS polyacrylamide gel electrophoresis) using a gradient gel (produced by Daiichi Pure Chemicals Co., Ltd.) and a molecular weight marker (produced by Bio-Rad Lab.). The molecular weight was calculated to be 43 kD.

(f) Amino acid composition:

The present enzyme was isolated by SDS-PAGE, and transferred onto a PVDF membrane (produced by Milipore) by using a semidry blotting device (produced by Milipore). The resultant membrane was stained with Coomassie Brilliant Blue, and a visual portion corresponding to the present enzyme was cut out with a razor. The extract of the portion was subjected to an amino acid analysis by HPLC using a picotag column (produced by Water Co., Ltd.). The results are shown in Table 1 below. Table 1 also shows the amino acid composition calculated from the amino acid sequence determined based upon the DNA sequence of the present enzyme described in detail below.

TABLE 1

| Amino acid | Mole of Amino acid/mole of protein (%) | Found | Calculated |
|---|---|---|---|
| ASX | 10.2 | 39.1 | 39 |
| GLX | 10.2 | 39.2 | 38 |
| SER | 4.4 | 17.1 | 22 |
| GLY | 8.2 | 31.4 | 33 |
| HIS | 2.0 | 7.7 | 12 |
| ARG | 2.8 | 10.8 | 12 |
| THR | 4.9 | 18.8 | 26 |
| ALA | 13.2 | 50.6 | 53 |
| PRO | 4.2 | 16.1 | 16 |
| TYR | 1.4 | 5.3 | 3 |
| VAL | 9.7 | 37.1 | 36 |
| MET | 2.2 | 8.4 | 8 |
| CYS | 0.0 | 0.0 | 1 |
| ILE | 5.5 | 21.0 | 17 |
| LEU | 13.3 | 50.9 | 41 |
| PHE | 3.6 | 13.8 | 11 |
| TRP | — | 0.0 | 3 |
| LYS | 4.4 | 16.7 | 17 |
| Total | 100.0 | 384.0 | 388 |

(5) Determination of the DNA sequence encoding the norbornane type ester hydrolase:

The determination of the DNA sequence of a DNA fragment including DNA encoding the norbornane type ester hydrolase of the present invention is exemplified as follows: The sequence of the DNA fragment can be determined by analyzing the genomic DNA of *Acetobacter pasteurianus*.

(A) Cloning by the shotgun method:

Cells of *Acetobacter pasteurianus* are collected and treated with SDS. The resulting lysate is subjected to cesium chloride - ethidium bromide equilibrium density-gradient centrifugation to obtain chromosome DNA. The chromosome DNA is cleaved with an appropriate restriction enzyme. Each fragment of the cleaved DNA is inserted into a vector DNA that has been previously cleaved with the same kind of restriction enzyme, or inserted, through a linker, into a vector that has been previously cleaved with an appropriate restriction enzyme. Thus, recombinant plasmids are produced. Such a vector can be, for example, pBR322 (produced by Takara Shuzo Co., Ltd.). The plasmids produced in this manner are then introduced into host cells. A preferable host is *E. coli*, particularly, *E. coli* JM109 ATCC 53323. The recombinant plasmids are introduced into host cells, for example, in accordance with the method described by Hanahan, et al. (J. Mol. Biol., 166, 557–580 (1983)).

(B) Selection of a clone including the gene of the norbornane type ester hydrolase:

A clone including the gene of the norbornane type ester hydrolase in the obtained transformant is screened as follows. The transformant is subject to a plate culture. The colonies grown thereon are transferred onto a filter paper. The filter paper is soaked with an esterase detection solution which is a 50 mM phosphate buffer (pH 7.0) including 0.1% β-naphthyl acetate and 0.02% Fast Blue BB. As a result, the color of the colony in which esterase is produced is purplish red. Thus, a colony whose color has changed into purplish red is selected.

Such a colony is cultured, and allowed to react with 1% (±)-exo-norbornyl acetate. The product is analyzed by optical resolution gas chromatography using the method described in item 4a. In this manner, it is determined that the clone that has produced (−)-norborneol is a clone including the gene of the norbornane type ester hydrolase.

(C) Determination of the base sequence of an insert:

The base sequence of an insert of a recombinant plasmid is determined, for example, as follows: The insert is cleaved at a restriction enzyme site therein, and the obtained DNA fragments are respectively cloned with appropriate vectors for sequence determination. The base sequence of each of the cloned fragments is determined by the Sanger method (Sanger et al., Proc. Natl. Acad. Sci. U.S.A., 74, 5463–5467 (1977)). Thus, the entire base sequence of the insert can be determined.

(6) Construction of an expression vector including the gene of the norbornane type ester hydrolase:

The gene of the norbornane type ester hydrolase of the present invention is inserted into an appropriate vector such as pUC119 and pBR322 (produced by Takara Shuzo Co., Ltd.) to serve as an expression vector for expressing the norbornane type ester hydrolase.

(7) Formation of a transformant and production of the norbornane type ester hydrolase:

The above-mentioned expression vector is introduced into a host cell such as E. coli, yeast and an animal cell to form a transformant. By culturing the transformant, the norbornane type ester hydrolase of the present invention can be produced. The hydrolase is obtained as follows.

The transformant is cultured, and the culture is subjected to centrifugation to collect the cells of the bacteria therein. The collected cells are washed with a buffer, and suspended in, for example, an equal volume of a 0.1M phosphate buffer (pH 7.0) to obtain a cell suspension. The cells in the suspension are disrupted mechanically or ultrasonically. The supernatant of the resultant suspension is obtained by centrifugation as a crude enzyme solution.

The norbornane type ester hydrolase of the present invention can be purified by various methods. An example of the methods includes the following.

Ammonium sulfate is added to the crude enzyme solution so as to achieve 30% saturation. The precipitate is removed from the mixture, and ammonium sulfate is further added thereto so as to achieve 70% saturation. The precipitate in the mixture is collected. The dialyzed solution of the collected precipitate is subjected to ion exchange chromatography using a DEAE Sepharose fast flow column and successively gel filtration using a Sephacryl S-200 column to collect an active fraction. The fraction is subjected to polyacrylamide gel electrophoresis by using a device produced by Marysol Industries. The activity of the resultant fraction is analyzed by the method described in item 5B, and the active portion is cut out. The portion is crushed and eluted into a buffer to obtain an enzyme of high purity.

Any of the culture broth, the cell suspension, the crude enzyme and the purified enzyme obtained in the above procedures can be used in the enzymatic reaction.

(8) Optically selective hydrolysis of the (±)-exo-norbornane type ester:

The (±)-exo-norbornane type ester is optically selectively hydrolyzed by using the culture broth, the cell suspension, the crude enzyme or the purified enzyme obtained in item 7. For example, the reaction is conducted in a buffer by mixing the (±)-exo-norbornane type ester with the enzyme in one of the above forms at a temperature of 30° C. for 10 minutes. Then, chloroform is added to the reaction mixture, and the substrate and product are extracted. The extract is analyzed by gas chromatography using, for example, a column for optical resolution (produced by J & W Scientific). Thus, it is confirmed that the optically active norborneol is produced from the enzyme in any of the above forms.

EXAMPLES

The present invention will now be described in more detail by way of examples.

Example 1

Isolation and Purification of a Norbornane Type Ester Hydrolase

A norbornane type ester hydrolase of the present invention was produced from Acetobacter pasteurianus ATCC 12873, and was isolated and purified as follows. Seventy liters of a medium (pH 7.0) containing 0.5% glucose, 1.0% peptone, 1.0% yeast extract, 0.5% glycerin and 1.0% calcium carbonate was charged in a 100 liter jar fermentor, and sterilized. A seed culture of Acetobacter pasteurianus ATCC 12873, which had been previously cultured in a medium (pH 7.0) containing 0.5% glucose, 1.0% peptone, 1.0% yeast extract and 0.5% glycerin, was inoculated thereto so as to make the volume of seed culture up to 4% of the entire medium. The cultivation was conducted at a temperature of 28° C. for 48 hours, and the culture, i.e., cell suspension, was centrifuged to collect the bacteria cells therein. The collected bacteria cells were washed twice with a 0.1M phosphate buffer (pH 7.0) and suspended in 1.1 liter of a 0.1M phosphate buffer. The suspension was treated three times with a pressure type cell crusher (produced by Goulin Corp.; Manton-Goulin Laboratory homogenizer) to crush the cells therein. The resultant was centrifuged and the supernatant was obtained.

Ammonium sulfate was added to the supernatant so as to achieve 30% saturation, and the mixture was stirred on ice for 1 hour and centrifuged to obtain the supernatant. Ammonium sulfate was added to this supernatant so as to achieve 70% saturation, and the mixture was stirred on ice for 1 hour and centrifuged to collect the precipitate. The precipitate was dissolved in 320 ml of a 0.1M phosphate buffer (pH 7.0), and the resultant solution was dialyzed against a 0.01M phosphate buffer (pH 7.0) at 8° C. overnight.

To the dialysate, 1 liter of distilled water and 250 g of DEAE Sepharose fast flow (produced by Pharmacia) were successively added, and the mixture was stirred at room temperature for 1 hour. The resulting Sepharose resin was washed with 2 liters of a 0.01M phosphate buffer (pH 7.0), and was packed into a column to elute an active fraction with a 0.01M phosphate buffer (pH 7.0) containing 0.3M sodium chloride. The eluted fraction was concentrated by using an ultrafiltration device (produced by Tosoh Corp.). The concentrate was loaded onto a column that had been previously charged with Sephacryl S-200 (produced by Pharmacia), equilibrated with a 50 mM Tris-HCl buffer, thereby eluting the concentrate with 50 mM tris-HCl buffer. The eluted fraction was collected and concentrated by the ultrafiltration.

The resulting concentrated solution was subjected to 10% polyacrylamide gel electrophoresis using a device produced by Marysol Industries. After the electrophoresis, the obtained gel was subjected to the esterase activity staining method of Higerd and Spizizen (J. Bacteriol. 114, 1184–1192 (1973)) as follows. The gel was dipped in 20 ml of a 0.1M phosphate buffer (pH 7.0) including 10 mg β-naphthyl acetate and 10 mg of Fast Blue RR to detect an active portion which changed its color to purplish red. The purplish red portion was cut out from the gel, finely crushed, and immersed in 100 ml of a 0.1M tris-HCl buffer at 4° C. overnight to elute an active protein. The procedure was repeated 10 times to obtain 1 liter of the eluted solution. The eluted solution was concentrated by ultrafiltration to achieve a final volume of 10 ml.

Example 2

Measurement of the Activity of the Norbornane Type Ester Hydrolase and Its Properties The norbornane type ester hydrolase reacts with p-nitrophenyl acetate as well as with exo-norbornane type ester as a substrate. The reaction with p-nitrophenyl acetate produces a colored material, p-nitrophenol. Since p-nitrophenol can be detected spectrophotometrically, the enzymatic activity of the norbornane type ester hydrolase was measured by the pNPA method in which p-nitrophenyl acetate was used as a substrate. Specifically, the reaction was conducted at 30° C. in 3 ml of a reaction mixture comprising 0.02% p-nitrophenyl acetate, a 0.1M phosphate buffer (pH 7.0) containing 5 mM magnesium chloride, and the enzyme solution obtained in Example 1. Free p-nitrophenol was quantified by measuring the absorbance at 400 nm by a spectrophotometer. The amount of enzyme necessary to produce 1 µmole of p-nitrophenol for 1 minute was defined as 1 unit (U). As a result, the activity of the enzyme purified in Example 1 was found to be 38.7 U/ml. Further, the amount of protein measured by a protein assay kit (produced by Bio-Rad Lab.) was 0.25 mg/ml.

The purified enzyme was analyzed in accordance with the method of Laemmli (Nature, 227, 680–685 (1970)) by SDS-PAGE using a gradient gel (produced by Daiichi Pure Chemicals Co., Ltd. ) and a molecular weight marker (produced by Bio-Rad Lab. ). As a result, the main band was found at a position corresponding to a molecular weight of 43 kD. Further, the enzyme was analyzed by HPLC using HPLC molecular weight markers (produced by Oriental Yeast Co., Ltd.) and a molecular weight measuring column (produced by Waters Co., Ltd.; PROTEINPAK-300). In this analysis, the active portion was eluted at a position also corresponding to a molecular weight of 43 kD. Therefore, it was indicated that the norbornane type ester hydrolase existed as a monomer.

The principal properties of the enzyme were found as follows:

(1) Appropriate reaction temperature and optimal pH:

The above-mentioned enzymatic activity measurement was performed by using p-nitrophenyl acetate as a substrate at various pH values. As a result, the optimal pH was found to be approximately 8. Further, the enzymatic activity measurement was also performed at various temperatures to find the appropriate reaction temperature to be approximately 50° C.

(2) Heat stability and a stable pH range:

One ml of the enzyme solution including a 0.1M phosphate buffer (pH 7.0) was allowed to stand for 2 hours at various temperatures, and then subjected to the above-mentioned activity measurement. As a result, the enzyme was found to be stable at a temperature up to 40° C. under the above-mentioned conditions. Furthermore, 1 ml of the enzyme solution including a 0.1M buffer at various pH values was allowed to stand at 30° C. for 1 hour, and then subjected to the activity measurement. As a result, the enzyme was found to be stable in a pH range of 6 to 8.

(3) Effect of inhibitors:

The above-mentioned activity measurement was performed with regard to 0.5 ml of the enzyme solution of 0.1M phosphate buffer (pH 7.0) containing 5 mM of one of the following inhibitors: ethylenediaminetetraacetic acid (EDTA), phenylmethylsulfonylfluoride (PMSF), N-tosyl-L-phenylalanyl chloromethyl ketone (TPCK), N-tosyl-L-lysyl chloromethyl ketone (TLCK), diisopropyl fluorophosphate (DFP), N-ethylmaleimide and iodoacetic acid. The enzyme solutions, including the respective inhibitors, were allowed to stand at 30° C. for 2 hours. As a result, the present enzyme was found to be completely inhibited by PMSF.

(4) Stability in solvents:

The activity measurement was performed with regard to 0.2 ml of the enzyme solution of 0.1M phosphate buffer (pH 7.0) containing one of the following solvents at a concentration of 30%: ethanol, methanol, acetonitrile, acetone, dimethyl sulfoxide (DMSO), N, N-dimethylformamide, 1,4-dioxane, ethyl acetate and trichloromethane. The enzyme solutions including the respective solvents were allowed to stand at 30° C. for 1 hour. As a result, the present enzyme exhibited 80% or more activity in methanol, DMSO or ethyl acetate at a concentration of 30%.

(5) Optically selective hydrolysis of the norbornane type ester:

The purified enzyme obtained in Example 1 was allowed to come in contact with various kinds of 1% (±)-exo-norbornane type esters respectively including formyl, acetyl, propionyl, n-butyryl and isobutyryl as the acyl R in formula I. The reaction was conducted at 30° C. for 30 minutes. The resultant was extracted with an equal volume of chloroform. The extract was analyzed by gas chromatography using a column for optical resolution (produced by J & W Scientific). As is apparent from the results shown in Table 2, (−)-norborneol was enantio-selectively produced from any of the esters.

TABLE 2

| Acyl R in the norbornane | Produced norborneol (mg/ml) | |
|---|---|---|
| type ester Formula I | (−)-isomer | (+)-isomer |
| Formyl | 1.49 | 0.15 |
| Acetyl | 2.48 | 0.19 |
| Propionyl | 3.39 | 0.45 |
| n-butyryl | 2.30 | 0.29 |
| isobutyryl | 2.76 | 0.69 |

Example 3

Cloning of the Gene of the Norbornane Type Ester Hydrolase from *Acetobacter pasteurianus*

(1) Cloning by the shotgun method:

Cells of Acetobacter pasteurianus in a culture medium were collected, and treated with 1% SDS to obtain a lysate. The lysate was subjected to cesium chloride - ethidium bromide equilibrium density-gradient centrifugation, thereby obtaining purified chromosomal DNA. Approximately 100 units of a restriction enzyme BamHI was added to 10 µg of the DNA, and the reaction was conducted at 37° C. for 120 minutes. The resultant mixture was incubated at 70° C. for 5 minutes to inactivate the restriction enzyme, and ethanol precipitation was performed to collect the DNA. The obtained DNA fragments, cleaved with the restriction enzyme BamHI, were dissolved in 10 µl of TE buffer of 10 mM Tris-HCl (pH 8.0) including 1 mM EDTA.

A vector pBR322 (produced by Takara Shuzo Co., Ltd. ) was used as a cloning vector. Approximately 50 units of the restriction enzyme BamHI was added to 5 µg of the vector pBR322, and the reaction was conducted at a temperature of 37° C. for 2 hours. The reaction mixture was precipitated with ethanol to collect the DNA. The collected DNA was dissolved in a buffer (pH 8.0) including 50 mM of Tris-HCl and 1 mM magnesium chloride. Approximately 20 units of bacterial alkaline phosphatase (BAP) was added thereto, and the reaction was conducted at 37° C. for 1 hour. The resultant reaction mixture was extracted with an equal volume of a phenol solution. Ethanol was added to the obtained aqueous layer to precipitate the DNA. The collected DNA was dissolved in 10 µl of TE buffer.

Five μl of the obtained solution including the fragments of the chromosome of *Acetobacter pasteurianus*, cleaved with the restriction enzyme BamHI, was mixed with 1 μl of a solution including the vector pBR322 cleaved and dephosphorylated with the restriction enzyme BamHI and BAP. Ligation was achieved with a commercially available kit (produced by Takara Shuzo Co., Ltd.; DNA Ligation Kit) to produce a recombinant DNA. Using the recombinant DNA, *E. coli* JM109 ATCC 53323 was transformed in accordance with the method of Hanahan et al. (J. Mol. Biol., 166, 557–580 (1983)). The transformant was cultured on an L agar medium (pH 7.3) (i.e., a medium including 1% bacto tryptone, 0.5% yeast extract, 0.5% sodium chloride and 1.8% agar) including 50 μg/ml of ampicillin, whereby colonies of the transformant were formed.

(2) Selection of the clone:

The activity staining method of Example 1 was used to select a colony having an esterase activity among the colonies formed in item 1 above. Specifically, the colonies formed on the L agar medium were replicated onto a filter paper. The filter paper was soaked with an esterase detection solution which is a 50 mM phosphate buffer ( pH 7.0 ) including 0.1% β-naphthyl acetate and 0.02% Fast Blue BB to obtain a purplish red colony exhibiting esterase activity. Through this procedure, 17 purplish red colonies were detected and isolated from approximately 7,800 colonies.

Such an positive colony was cultured overnight by using 5 ml of an L broth including 50 μg/ml of ampicillin to react with 1% exo-norbornyl acetate. As a result, norborneol was produced. In this manner, the strain forming the positive colony was confirmed to be a clone including the gene of the norbornane type ester hydrolase.

From the cell of the strain producing the hydrolase, plasmids were isolated by the method of Birnboim et al. (Nucleic Acids Res., 7, 1513–1523 (1979)). The plasmids were cleaved with the restriction enzymes BamHI, EcoRI, HindIII and PstI. The resultant recombinant plasmids were analyzed by agarose gel electrophoresis. As a result, it was found that a fragment of 4.5 kb was inserted in the same direction in all of the plasmids. One of the plasmids was designated as pBNA21.

Figure 2:
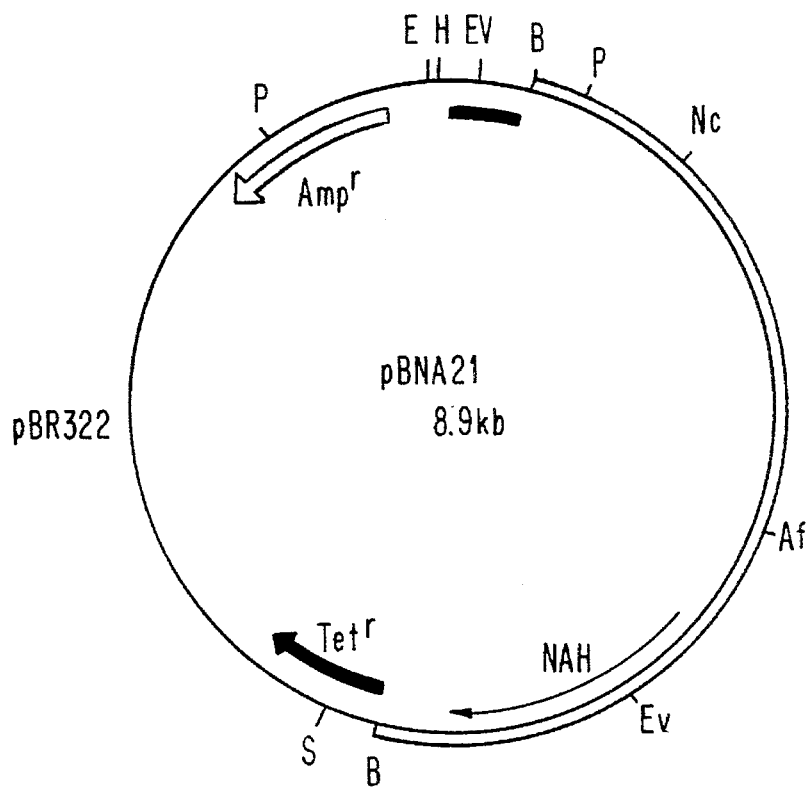
FIG. 2 is a restriction map of a plasmid pBNA21 including the structural gene of the norbornane type ester hydrolase of the present invention.

(3) Preparation of the restriction map of the plasmid and minimization of the plasmid:

The recombinant plasmid pBNA21 was cleaved with various restriction enzymes to construct a restriction map. The resulting restriction map is shown in FIG. 2. The abbreviations used in this figure indicate sites to be cleaved with the following restriction enzymes:

E: EcoRI

H: HindIII

EV: EcoRV

B: BamHI

P: PstI

Nc: NcoI

Af: AflII

S: SalI

Further, in order to determine the location of the gene encoding the norbornane type ester hydrolase, deletions and frameshift mutations of an exogenous DNA fragment of 4.5 kb were prepared by using the restriction enzymes BamHI, HindIII, AflII, NcoI and SalI. The resultant DNA fragments were analyzed by the esterase activity staining method of item 2 to find whether or not they had the enzymatic activity of the norbornane type ester hydrolase. As a result, it was found that only the plasmid in which an AflII-SalI fragment of 2.4 kb was deleted did not exhibit the activity. This result revealed that the gene of the norbornane type ester hydrolase of the present invention was located in a region of 2.1 kb between AflII and BamHI that corresponds to the AflII-SalI fragment of 2.4 kb excluding 0.3 kb between BamHI and SalI derived from the vector.

Then, the plasmid pBNA21 was cleaved with the restriction enzyme AflII, blunt ended with T4 DNA polymerase, and then cleaved with the restriction enzyme BamHI. The resultant reaction mixture was subjected to agarose gel electrophoresis to obtain a DNA fragment of 2.1 kb by using a commercially available kit (produced by BIO101; GENECLEAN).

Figure 3:
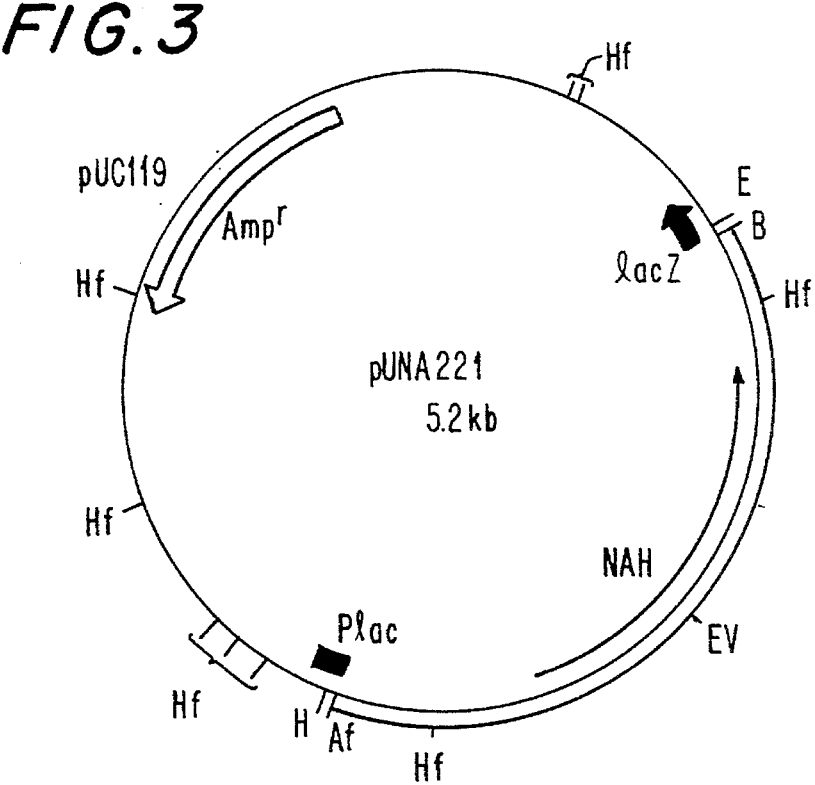
FIG. 3 is a restriction map of a plasmid pUNA221 including the structural gene of the norbornane type ester hydrolase of the present invention.

A vector pUC119 (produced by Takara Shuzo Co., Ltd.) was cleaved at BamHI and HincII cleavage sites existing at a multicloning site of the lacZ gene in the vector. The DNA fragment of 2.1 kb was ligated with the resultant vector fragment so that the fragment is aligned in the same direction as that of the lac promoter of the vector pUC119. Since the blunt ended AflII cleavage site was ligated with the HincII cleavage site, the AflII cleavage site was regenerated. *E. coli* JM109 was transformed by using the obtained recombinant plasmid, and the resulting transformant was cultured to form colonies having the activity of the norbornane type ester hydrolase. The recombinant plasmid produced in this manner was designated as pUNA221. The restriction map of pUNA221 is shown in FIG. 3.

Example 4

Determination of the Base Sequence of the Gene of the Norbornane Type Ester Hydrolase, and Identification of the Structural Gene of the Norbornane Type Ester Hydrolase The DNA base sequence of the AflII-BamHI fragment of 2.1 kb in the recombinant plasmid pUNA221 produced in Example 3 was determined by the method of Sanger et al. (Proc. Natl. Acad. Sci. U.S.A., 74, 5463–5467 (1977)). As a result, an open reading frame (ORF) encoding a protein comprising 388 amino acids including methionine corresponding to the starting codon ATG was found.

The AflII-BamHI fragment of 2.1 kb was then cleaved with a restriction enzyme HinfI to obtain a fragment of 1.5 kb including the ORF that was regarded as encoding the norbornane type ester hydrolase. The obtained fragment was inserted into a plasmid pUC119 at the HincII cleavage site in the same direction as that of the lac promoter, thereby producing a plasmid pUNA-Hf.

*E. coli* JM109 was transformed by using the plasmid pUNA-Hf. When the obtained transformant was analyzed by the activity staining method described in item 2 of Example 3, the color of the colony was changed into purplish red to exhibit esterase activity. Then, the transformant was mixed with a 1% (±)-exo-norbornyl acetate mixture and allowed to stand at 30° C. for 10 minutes. The resulting mixture was analyzed by the method described in item 5 of Example 2. As a result, it was found that 1.68 mg/ml of (−)-exo-norborneol and 0.15 mg/ml of (+)-exo-norborneol were produced. Thus, the optical selectivity was confirmed to be as high as that of the enzyme derived from *Acetobacter pasteurianus* obtained in Example 1.

Example 5

Expression of the Norbornane Type Ester Hydrolase in *E. coli*

(1) Expression of the norbornane type ester hydrolase

The plasmid pUNA-Hf obtained in Example 4 was introduced into *E. coli* JM103 ATCC 39403 to produce a transformant JM103/pUNA-Hf.

The transformant JM103/pUNA-Hf, which was previously cultured in an L broth including 50 μg/ml of ampicillin, was inoculated into 50 ml of the same medium in a 500 ml flask so that the inoculum size of the transformant was 1% of the entire medium, and was cultured at 37° C. with shaking. When $OD_{660}$ was 0.2, 1 mM isopropyl-β-D-galactopyranoside (IPTG) was added thereto. The cultivation was continued, and 6 hours after the addition of IPTG, the culture broth was obtained. The culture broth was frozen overnight, and melted to be used as a specimen for an activity measurement. The activity measured by the pNPA method was 68 units per 1 ml of the culture broth. As a control, a strain including the plasmid pUC119 alone was cultured in the same manner as above. The activity of the control was 0.2 unit per 1 ml of the culture solution.

(2) Optically selective deacetylation of exo-norbornyl acetate:

(±)-Exo-norbornyl acetate used as a substrate was optically selectively deacetylated by *E. coli* JM103 including the plasmid pUNA-Hf as follows. The bacterial cells were collected from the cultured broth of *E. coli* JM103/pUNA-Hf as mentioned above by centrifugation, and suspended in an equal volume of a 0.1M phosphate buffer (pH 7.0). Then, 1% (±)-exo-norbornyl acetate was added to 1.5 ml of the obtained suspension, and the reaction was conducted at 30° C. for 15 minutes. The resultant reaction mixture was analyzed by the method described in item 5 of Example 2. As a result, it was found that 1.91 mg/ml of (−)-exo-norborneol and 0.15 mg/ml of (+)-exo-norborneol were produced.

Examples of the usage of the optically active norborneol produced from the norbornane type ester hydrolase of the present invention will now be described as Reference Examples.

Reference Example 1

By the use of a norbornane type ester hydrolase obtained in Example 1, (−)-(1S, 2S, 4R)-exo-norborneol was produced according to the method of item 5 in Example 2. Then, 2.8 g (0.025 mole) of the obtained (−)-(1S, 2S, 4R)-exo-norborneol was dissolved in 56 ml of methylene chloride, and 8.1 g (1.5 mole) of pyridinium chlorochromate (PCC) and 1 g of molecular sieve 4A were added thereto. The reaction was conducted at a temperature of 25° C. to 30° C. for 1 hour. Then, the reaction mixture was diluted with 56 ml of toluene, and the resultant was allowed to pass through a column of 28 g silica gel to remove insoluble materials. The eluate was concentrated and dried to give crude (+)-norcamphor as a white crystal line powder. The obtained (+)-norcamphor was dissolved in 45 ml of tetrahydrofuran, and the resultant solution was added dropwise to a 30 ml tetrahydrofuran solution including 1.1 mole of Lithium diisopropyl amide (LDA) at a temperature of −10° C. to −15° C. The reaction was conducted at the same temperature for 20 minutes, and 3.3 g (1.1 molar ratio) of allyl bromide was added dropwise thereto at 0° C. or lower. Then, the reaction was conducted at room temperature for 3 hours. The reaction mixture was poured into 70 ml of ice water, and the resultant mixture was made acidic with a diluted hydrochloric acid solution. The acidic solution was extracted with 50 ml of toluene twice. The combined toluene layer was washed with water, and the solvent was removed in vacuo to give crude (+)-exo-3-(2-propenyl)-bicyclo[2.2.1]heptan-2-one as an oily residue. The residue was distilled in vacuo to obtain a fraction having a boiling point of 92° C.–103° C. at 10–12 mmHg. Yield: 3.07 g (82%). Chemical purity (GC): 98.6%. Endo isomer: 0.4%. Optical purity (HPLC): 90% ee. Specific rotation $[\alpha]^{25}D+84.6°$ (C=1.0, $CHCl_3$).

Reference Example 2

The similar procedure to Example 5 was carried out on a large scale, and a reaction mixture including a major amount of (−)-(1S, 2S, 4R)-exo-norborneol and a minor amount of (+)-(1R, 2R, 4S)-exo-norborneol was obtained. The similar procedure to that described in Reference Example 1 was repeated with the use of this mixture. Thus, a crude (+)-exo-3-(2-propenyl)-bicyclo[2.2.1]heptan-2-one was obtained. The crude product was distilled in vacuo to obtain a fraction having a boiling point of 74° C.–86° C. at 3–4 mmHg which is a purified (+)-exo-3-(2-propenyl)-bicyclo[2.2.1]heptan-2-one. Yield: 1.38 g (78%). Chemical purity (GC): 98.8%. Endo isomer: 0.9%. Optical purity (HPCL): 98% ee. Specific rotation $[\alpha]^{25}D+89°$ (C=1.286, $CHCl_3$). IR (Film) 3060, 1740, 1640, 1460, 1440, 1310, 1090 $cm^{-1}$. $^1HNMR$ ($CDCl_3$) δ 1.30–2.00 (m, 8H), 2.5–2.6 (m, 3H) δ 4.90–5.20 (m, 2H), 5.7–5.9 (m, 1H).

The compounds obtained in the Reference Examples can be used to produce a $TXA_2$ receptor antagonist that is useful as a medicament by the method described for example, in J. Med. Chem. 31(9), 1847–1854 (1988).

As described above, the present invention provides a norbornane type ester hydrolase that enantio-selectively hydrolyzes a (±)-exo-norbornane type ester to produce optically active norborneol; a structural gene of the norbornane type ester hydrolase derived from *Acetobacter pasteurianus*; an expression vector including the structural gene; a transformant including the expression vector; and a production method for the norbornane type ester hydrolase using the transformant. The optically active norborneol produced by reacting the norbornane type ester hydrolase of the present invention with a (±)-exo-norbornane type ester can be synthesyzed into (±)-exo-3-(2-propenyl)-bicyclo[2.2.1]heptan-2-one, from which a medically useful $TXA_2$ receptor antagonist can be produced.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which will become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. An isolated or purified norbornane type ester hydrolase derived from a bacterium of the species *Acetobacter pasteurianus* that enantioselectively hydrolyzes a (±)-exo-norbornane type ester represented by Formula I:

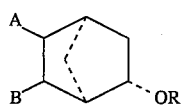
(I)

wherein R is acyl, and A and B are hydrogens, respectively, or where A and B are absent, resulting in a carbon-carbon double bond between the carbons to which A and B are attached in Formula I;

the norbornane type ester hydrolase having an optimal pH of approximately 8 and a stable pH range of approximately 6 to 8.

2. An isolated or purified norbornane type ester hydrolase derived from a bacterium of the species *Acetobacter pasteurianus* that enantioselectively deacetylates a (±)-exo-norbornyl acetate represented by Formula II:

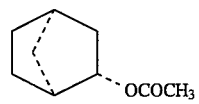
(II)

the norbornane type ester hydrolase having an optimal pH of approximately 8 and a stable pH range of approximately 6 to 8.

3. An isolated or purified norbornane type ester hydrolase according to claim 1, wherein the *Acetobacter pasteurianus* is *Acetobacter pasteurianus* ATCC 12873.

4. An isolated or purified norbornane type ester hydrolase according to claim 2, wherein the *Acetobacter pasteurianus* is *Acetobacter pasteurianus* ATCC 12873.

5. An isolated or purified norbornane type ester hydrolase comprising an amino acid sequence from Met in the 1 position to Ala in the 388 position of SEQ ID No. 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 1167 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Acetobacter pasteurianus
    ( B ) STRAIN: ATCC 12873

( i x ) FEATURE:
    ( A ) NAME/KEY: CDS
    ( B ) LOCATION: 1..1164

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | TCC | AAC | ACC | ATT | ACA | GCA | CTC | ACC | ATG | CCC | AAG | TTC | GGT | TTG | GCC | 48 |
| Met | Ser | Asn | Thr | Ile | Thr | Ala | Leu | Thr | Met | Pro | Lys | Phe | Gly | Leu | Ala | |
| 1 | | | | 5 | | | | | 10 | | | | | 15 | | |
| ATG | ACA | GAA | GGC | AAG | CTG | GCA | TCA | TGG | ACA | GTA | TCT | GTT | GGC | CAG | AGC | 96 |
| Met | Thr | Glu | Gly | Lys | Leu | Ala | Ser | Trp | Thr | Val | Ser | Val | Gly | Gln | Ser | |
| | | | 20 | | | | | 25 | | | | | 30 | | | |
| GTG | CAG | CAG | GGT | GAT | GAA | CTG | GCG | GAT | ATT | GAA | ACC | ACC | AAA | ATT | ACC | 144 |
| Val | Gln | Gln | Gly | Asp | Glu | Leu | Ala | Asp | Ile | Glu | Thr | Thr | Lys | Ile | Thr | |
| | | 35 | | | | | 40 | | | | | 45 | | | | |
| AGC | AGT | TAT | GAA | AGC | CCC | GCC | GCA | GGT | GTG | CTG | CGC | AAA | CAG | GTG | GCC | 192 |
| Ser | Ser | Tyr | Glu | Ser | Pro | Ala | Ala | Gly | Val | Leu | Arg | Lys | Gln | Val | Ala | |
| | 50 | | | | | 55 | | | | | 60 | | | | | |
| GAG | GCG | GGG | GAA | ACC | CTG | CCC | GTG | GGC | GCA | CTG | ATT | GGT | GTT | TTG | GCA | 240 |
| Glu | Ala | Gly | Glu | Thr | Leu | Pro | Val | Gly | Ala | Leu | Ile | Gly | Val | Leu | Ala | |
| 65 | | | | | 70 | | | | | 75 | | | | | 80 | |
| GAT | GCC | GAA | ACG | CCA | GAT | GTG | GAT | ATT | GAA | GCC | TTT | ATC | AAA | AAC | TTT | 288 |
| Asp | Ala | Glu | Thr | Pro | Asp | Val | Asp | Ile | Glu | Ala | Phe | Ile | Lys | Asn | Phe | |
| | | | | 85 | | | | | 90 | | | | | 95 | | |
| CAT | GCA | GAA | AAC | CCA | CAG | GAT | GCG | GCT | GCA | ACA | GAA | GAT | GCC | TCT | GCC | 336 |
| His | Ala | Glu | Asn | Pro | Gln | Asp | Ala | Ala | Ala | Thr | Glu | Asp | Ala | Ser | Ala | |
| | | | 100 | | | | | 105 | | | | | 110 | | | |
| GGG | GAA | CCC | AAG | CAG | GTT | ACG | GTA | GGC | GAA | CAC | ACG | CTA | AAT | GTG | CGT | 384 |
| Gly | Glu | Pro | Lys | Gln | Val | Thr | Val | Gly | Glu | His | Thr | Leu | Asn | Val | Arg | |
| | | 115 | | | | | 120 | | | | | 125 | | | | |
| GAT | GTT | GGC | ACG | CAG | GAG | GGC | ACG | CCC | ATT | GTG | CTG | GTG | CAC | GGT | TTT | 432 |
| Asp | Val | Gly | Thr | Gln | Glu | Gly | Thr | Pro | Ile | Val | Leu | Val | His | Gly | Phe | |
| | 130 | | | | | 135 | | | | | 140 | | | | | |
| GGC | GGA | GAT | ATC | AGC | AAC | TGG | CTG | CTC | ACA | CAG | GAT | GCC | TTG | GCC | GCA | 480 |
| Gly | Gly | Asp | Ile | Ser | Asn | Trp | Leu | Leu | Thr | Gln | Asp | Ala | Leu | Ala | Ala | |
| 145 | | | | | 150 | | | | | 155 | | | | | 160 | |
| GAA | AGG | CGC | GTA | ATT | GCG | TTT | GAT | CTG | CCG | GGG | CAT | GGG | GCT | TCC | TCT | 528 |
| Glu | Arg | Arg | Val | Ile | Ala | Phe | Asp | Leu | Pro | Gly | His | Gly | Ala | Ser | Ser | |
| | | | | 165 | | | | | 170 | | | | | 175 | | |
| AAA | AAC | GTG | GGC | ACA | GGC | ACG | CTG | GCG | TTT | TTG | GCC | GGT | GTG | GTA | AGC | 576 |
| Lys | Asn | Val | Gly | Thr | Gly | Thr | Leu | Ala | Phe | Leu | Ala | Gly | Val | Val | Ser | |
| | | | 180 | | | | | 185 | | | | | 190 | | | |
| GAA | TTG | CTG | CAA | ACC | CTT | AAA | ATA | GAA | AAA | GCC | CAT | GTG | GTG | GGC | CAT | 624 |
| Glu | Leu | Leu | Gln | Thr | Leu | Lys | Ile | Glu | Lys | Ala | His | Val | Val | Gly | His | |
| | | 195 | | | | | 200 | | | | | 205 | | | | |

| | | | | | | | | | | | | | | | | |
|---|---|---|---|---|---|---|---|---|---|---|---|---|---|---|---|---|
| TCT | TTG | GGG | GGC | GGC | ATT | GCC | CTG | ACC | CTG | CTG | CGA | GAT | CAC | CCT | GAT | 672 |
| Ser | Leu | Gly | Gly | Gly | Ile | Ala | Leu | Thr | Leu | Leu | Arg | Asp | His | Pro | Asp | |
| | 210 | | | | | 215 | | | | | 220 | | | | | |
| CAG | GTT | GCC | AGC | CTG | AAC | CTT | TTG | GCC | CCA | GCC | GGG | TTG | GGT | AAG | GAT | 720 |
| Gln | Val | Ala | Ser | Leu | Asn | Leu | Leu | Ala | Pro | Ala | Gly | Leu | Gly | Lys | Asp | |
| 225 | | | | | 230 | | | | | 235 | | | | | 240 | |
| GTG | AAT | GCA | GAT | TTT | ATC | AGC | GCA | TTT | GTG | GAT | AGT | GAA | AGC | AGC | CGC | 768 |
| Val | Asn | Ala | Asp | Phe | Ile | Ser | Ala | Phe | Val | Asp | Ser | Glu | Ser | Ser | Arg | |
| | | | | 245 | | | | | 250 | | | | | 255 | | |
| GAT | ATG | AAG | GCT | GTT | TTG | CAA | ATG | CTG | GTG | TAT | AAC | AAA | GCC | CTA | GTG | 816 |
| Asp | Met | Lys | Ala | Val | Leu | Gln | Met | Leu | Val | Tyr | Asn | Lys | Ala | Leu | Val | |
| | | | 260 | | | | | 265 | | | | | 270 | | | |
| GGC | CGT | AAG | ATG | GTG | GAT | GCC | GTG | CTG | CGT | GCA | CGT | AGG | CTA | GAT | GGC | 864 |
| Gly | Arg | Lys | Met | Val | Asp | Ala | Val | Leu | Arg | Ala | Arg | Arg | Leu | Asp | Gly | |
| | | 275 | | | | | 280 | | | | | 285 | | | | |
| GCG | CGG | GAT | GCC | CTG | CAC | GTT | ATT | GCT | AAA | GCG | TGC | TTC | CCC | AAC | GGG | 912 |
| Ala | Arg | Asp | Ala | Leu | His | Val | Ile | Ala | Lys | Ala | Cys | Phe | Pro | Asn | Gly | |
| | 290 | | | | | 295 | | | | | 300 | | | | | |
| CAT | CAG | GCG | GAT | GAT | CTG | CAC | TCG | GTG | CTA | GCT | GGG | GCG | GAA | ACA | CCT | 960 |
| His | Gln | Ala | Asp | Asp | Leu | His | Ser | Val | Leu | Ala | Gly | Ala | Glu | Thr | Pro | |
| 305 | | | | | 310 | | | | | 315 | | | | | 320 | |
| ACC | CAG | ATT | TTC | TGG | GGC | AAG | GAA | GAT | GAA | ATT | CTT | TCT | GTC | TCC | AAC | 1008 |
| Thr | Gln | Ile | Phe | Trp | Gly | Lys | Glu | Asp | Glu | Ile | Leu | Ser | Val | Ser | Asn | |
| | | | | 325 | | | | | 330 | | | | | 335 | | |
| GCC | GCT | GGC | CTG | CCA | GAT | GTC | ATC | CCC | GTG | ACA | GTG | TAT | GAA | GAA | ACA | 1056 |
| Ala | Ala | Gly | Leu | Pro | Asp | Val | Ile | Pro | Val | Thr | Val | Tyr | Glu | Glu | Thr | |
| | | | 340 | | | | | 345 | | | | | 350 | | | |
| GGC | CAT | CTG | CCG | CAG | CTT | GAA | CAT | GCA | ACA | GAT | GTG | AAC | AAA | GCC | ATT | 1104 |
| Gly | His | Leu | Pro | Gln | Leu | Glu | His | Ala | Thr | Asp | Val | Asn | Lys | Ala | Ile | |
| | | 355 | | | | | 360 | | | | | 365 | | | | |
| GCC | CTG | TTT | GTA | AAA | GAC | CCC | GAA | GCC | GCG | CTG | AGC | ATG | GCC | CGG | ATG | 1152 |
| Ala | Leu | Phe | Val | Lys | Asp | Pro | Glu | Ala | Ala | Leu | Ser | Met | Ala | Arg | Met | |
| | 370 | | | | | 375 | | | | | 380 | | | | | |
| GAC | GCG | ACA | GCC | TAA | | | | | | | | | | | | 1167 |
| Asp | Ala | Thr | Ala | | | | | | | | | | | | | |
| 385 | | | | | | | | | | | | | | | | |

( 2 ) INFORMATION FOR SEQ ID NO:2:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ser | Asn | Thr | Ile | Thr | Ala | Leu | Thr | Met | Pro | Lys | Phe | Gly | Leu | Ala |
| 1 | | | | 5 | | | | | 10 | | | | | 15 | |
| Met | Thr | Glu | Gly | Lys | Leu | Ala | Ser | Trp | Thr | Val | Ser | Val | Gly | Gln | Ser |
| | | | 20 | | | | | 25 | | | | | 30 | | |
| Val | Gln | Gln | Gly | Asp | Glu | Leu | Ala | Asp | Ile | Glu | Thr | Thr | Lys | Ile | Thr |
| | | | 35 | | | | 40 | | | | | 45 | | | |
| Ser | Ser | Tyr | Glu | Ser | Pro | Ala | Ala | Gly | Val | Leu | Arg | Lys | Gln | Val | Ala |
| | 50 | | | | | 55 | | | | | 60 | | | | |
| Glu | Ala | Gly | Glu | Thr | Leu | Pro | Val | Gly | Ala | Leu | Ile | Gly | Val | Leu | Ala |
| 65 | | | | | 70 | | | | 75 | | | | | 80 | |
| Asp | Ala | Glu | Thr | Pro | Asp | Val | Asp | Ile | Glu | Ala | Phe | Ile | Lys | Asn | Phe |
| | | | | 85 | | | | | 90 | | | | | 95 | |

-continued

| | | | | | | | | | | | | | |
|---|---|---|---|---|---|---|---|---|---|---|---|---|---|
| His | Ala | Glu | Asn 100 | Pro | Gln | Asp | Ala 105 | Ala | Thr | Glu | Asp | Ala 110 | Ser | Ala |
| Gly | Glu | Pro 115 | Lys | Gln | Val | Thr | Val 120 | Gly | Glu | His | Thr | Leu 125 | Asn | Val | Arg |
| Asp | Val 130 | Gly | Thr | Gln | Glu | Gly 135 | Thr | Pro | Ile | Val | Leu 140 | Val | His | Gly | Phe |
| Gly 145 | Gly | Asp | Ile | Ser | Asn 150 | Trp | Leu | Leu | Thr | Gln 155 | Asp | Ala | Leu | Ala | Ala 160 |
| Glu | Arg | Arg | Val | Ile 165 | Ala | Phe | Asp | Leu | Pro 170 | Gly | His | Gly | Ala | Ser 175 | Ser |
| Lys | Asn | Val | Gly 180 | Thr | Gly | Thr | Leu | Ala 185 | Phe | Leu | Ala | Gly | Val 190 | Val | Ser |
| Glu | Leu | Leu 195 | Gln | Thr | Leu | Lys | Ile 200 | Glu | Lys | Ala | His | Val 205 | Val | Gly | His |
| Ser | Leu 210 | Gly | Gly | Gly | Ile | Ala 215 | Leu | Thr | Leu | Leu | Arg 220 | Asp | His | Pro | Asp |
| Gln 225 | Val | Ala | Ser | Leu | Asn 230 | Leu | Leu | Ala | Pro | Ala 235 | Gly | Leu | Gly | Lys | Asp 240 |
| Val | Asn | Ala | Asp | Phe 245 | Ile | Ser | Ala | Phe | Val 250 | Asp | Ser | Glu | Ser | Ser 255 | Arg |
| Asp | Met | Lys | Ala 260 | Val | Leu | Gln | Met | Leu 265 | Val | Tyr | Asn | Lys | Ala 270 | Leu | Val |
| Gly | Arg | Lys 275 | Met | Val | Asp | Ala | Val 280 | Leu | Arg | Ala | Arg | Arg 285 | Leu | Asp | Gly |
| Ala | Arg 290 | Asp | Ala | Leu | His | Val 295 | Ile | Ala | Lys | Ala | Cys 300 | Phe | Pro | Asn | Gly |
| His 305 | Gln | Ala | Asp | Asp | Leu 310 | His | Ser | Val | Leu | Ala 315 | Gly | Ala | Glu | Thr | Pro 320 |
| Thr | Gln | Ile | Phe | Trp 325 | Gly | Lys | Glu | Asp | Glu 330 | Ile | Leu | Ser | Val | Ser 335 | Asn |
| Ala | Ala | Gly | Leu 340 | Pro | Asp | Val | Ile | Pro 345 | Val | Thr | Val | Tyr | Glu 350 | Glu | Thr |
| Gly | His | Leu 355 | Pro | Gln | Leu | Glu | His 360 | Ala | Thr | Asp | Val | Asn 365 | Lys | Ala | Ile |
| Ala | Leu 370 | Phe | Val | Lys | Asp | Pro 375 | Glu | Ala | Ala | Leu | Ser 380 | Met | Ala | Arg | Met |
| Asp 385 | Ala | Thr | Ala | | | | | | | | | | | | |